United States Patent [19]
Ludwig et al.

[11] Patent Number: 5,324,399
[45] Date of Patent: Jun. 28, 1994

[54] METHOD AND SYSTEM FOR MONITORING QUALITY OF PHOSPHATE COATING

[75] Inventors: Frank A. Ludwig, Rancho Palos Verdes; Bruce M. Eliash, Los Angeles, both of Calif.

[73] Assignee: Hughes Aircraft Company, Los Angeles, Calif.

[21] Appl. No.: 881,586

[22] Filed: May 12, 1992

[51] Int. Cl.$^5$ .......................................... G01N 27/26
[52] U.S. Cl. ................................ 204/153.1; 204/412; 204/434; 204/DIG. 8; 427/443.1; 427/435
[58] Field of Search ............. 204/153.1, 434, DIG. 8, 204/412; 427/443.1, 435

[56] References Cited

U.S. PATENT DOCUMENTS

| | | | |
|---|---|---|---|
| 2,132,439 | 10/1938 | Romig | 204/434 |
| 2,766,423 | 10/1956 | Barker | 324/440 |
| 3,841,988 | 10/1974 | Gleason | 204/196 |
| 4,019,129 | 4/1977 | Grau | 204/434 |
| 4,310,389 | 1/1982 | Harbulak | 204/434 |
| 4,500,391 | 2/1985 | Schmidt et al. | 204/406 |
| 4,631,116 | 12/1986 | Ludwig | 204/434 |
| 4,718,990 | 1/1988 | Hashimoto et al. | 204/434 |

FOREIGN PATENT DOCUMENTS

| | | |
|---|---|---|
| 0107491 | 5/1984 | European Pat. Off. |
| 8605881 | 10/1986 | PCT Int'l Appl. |
| 2153854 | 8/1985 | United Kingdom |

OTHER PUBLICATIONS

"Metal Surface Treatments (Chemical)" in Kirk-Othmer's Encyclopedia of Chemical Technology, third ed., pp. 304–308, (1981)*.

Freeman, "Phosphating and Metal Pretreatment-A Guide to Modern Process and Practice", Industrial Press, Inc., 1986*, Chapter 2.

Sadkowski et al, "Evaluation of the Effect of Surface Pretreatment on Metal Phosphating by Impedance Measurements", Proceedings of the Symposium on Advances in Corrosion Protection by Organic Coatings, Apr. 11–14, 1989*, Cambridge, England.

Zantout et al, "Electrochemical Acceleration of Phosphating Process" Transactions of the Institute of Metal Finishing, 1983*, vol. 61, pp. 88–92.

Primary Examiner—T. Tung
Attorney, Agent, or Firm—M. E. Lachman; M. W. Sales; W. K. Denson-Low

[57] ABSTRACT

A method and system for monitoring the quality of a phosphate coating on a metal surface having a large surface area. The method comprises applying a current or potential between the metal surface and one or more counter electrodes while they are in the phosphating solution and superimposing a constant ac signal thereon. An ac impedance spectra is obtained by measuring the ac potential between the metal substrate and one or more reference electrodes located between the counter electrode and the substrate. The ac impedance spectra provide an indication of defects in the phosphate coating even when the defects are located within a relatively small region of the total surface area of the metal surface.

17 Claims, 13 Drawing Sheets

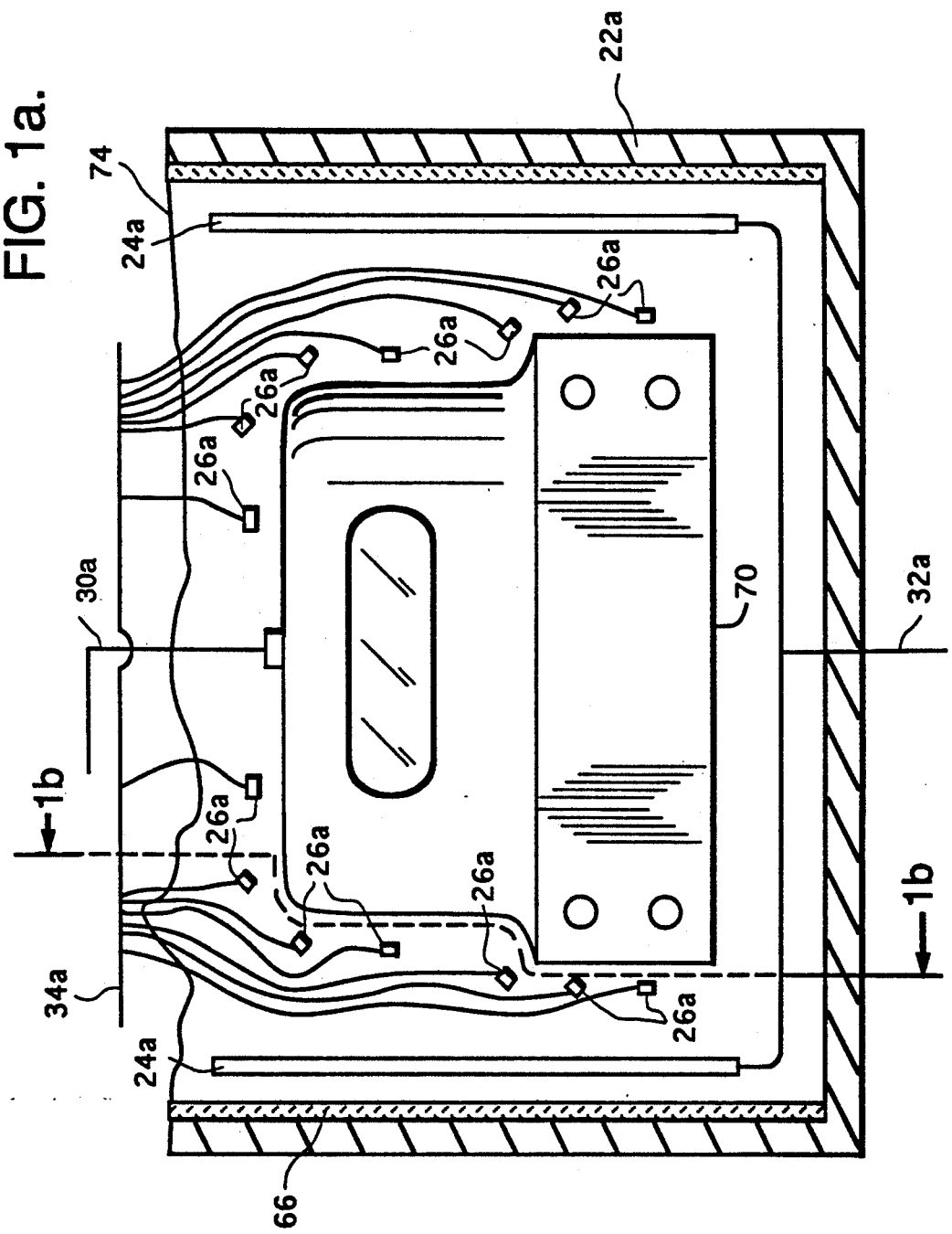

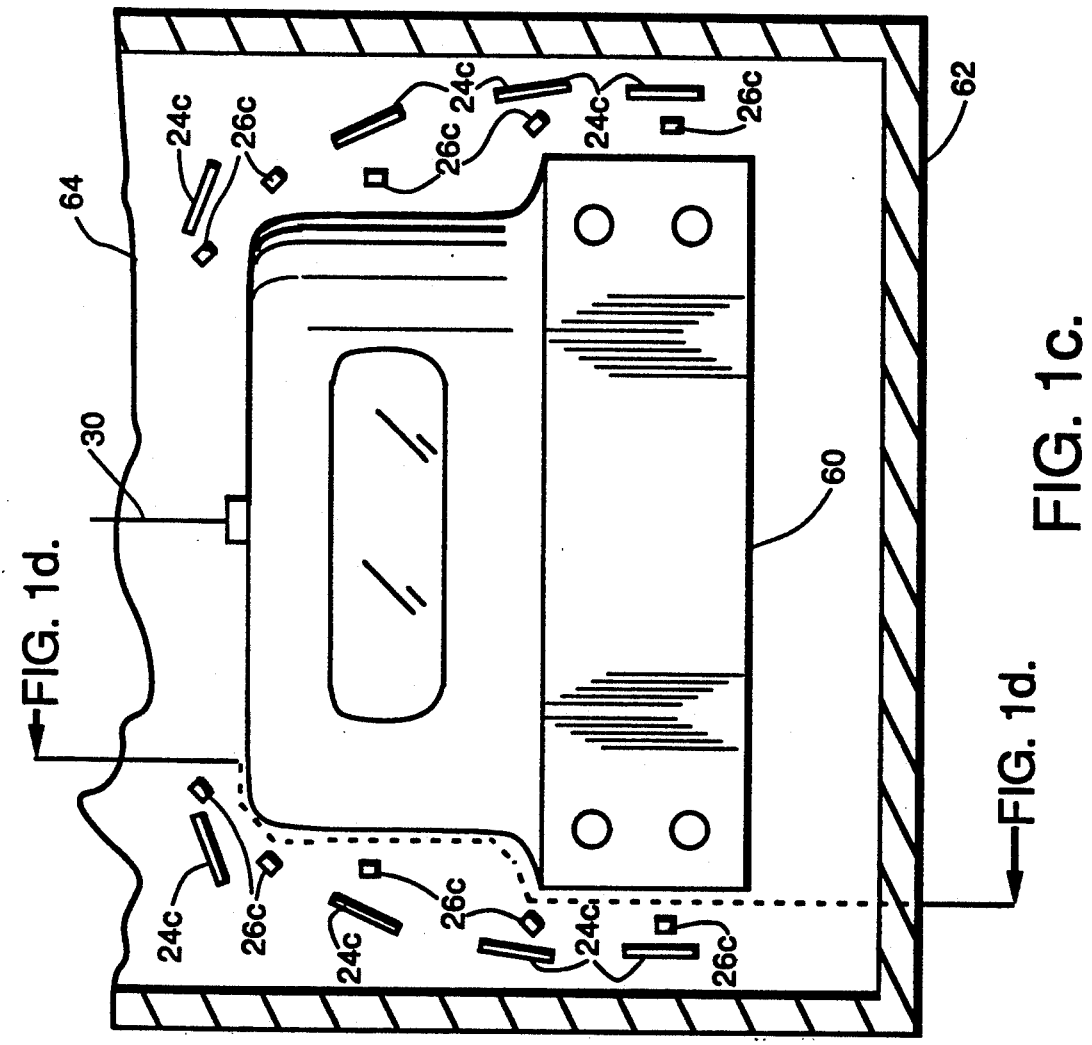

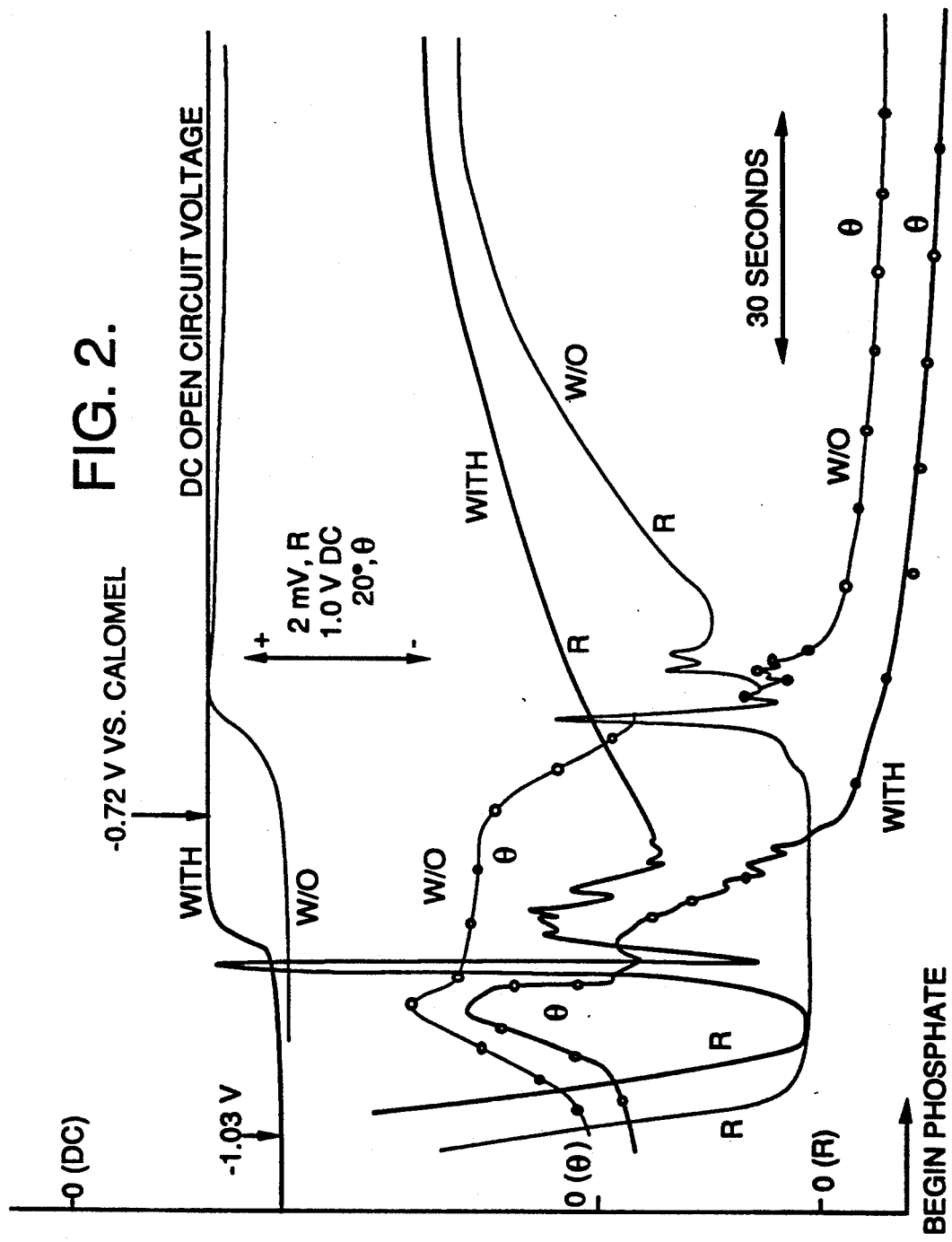

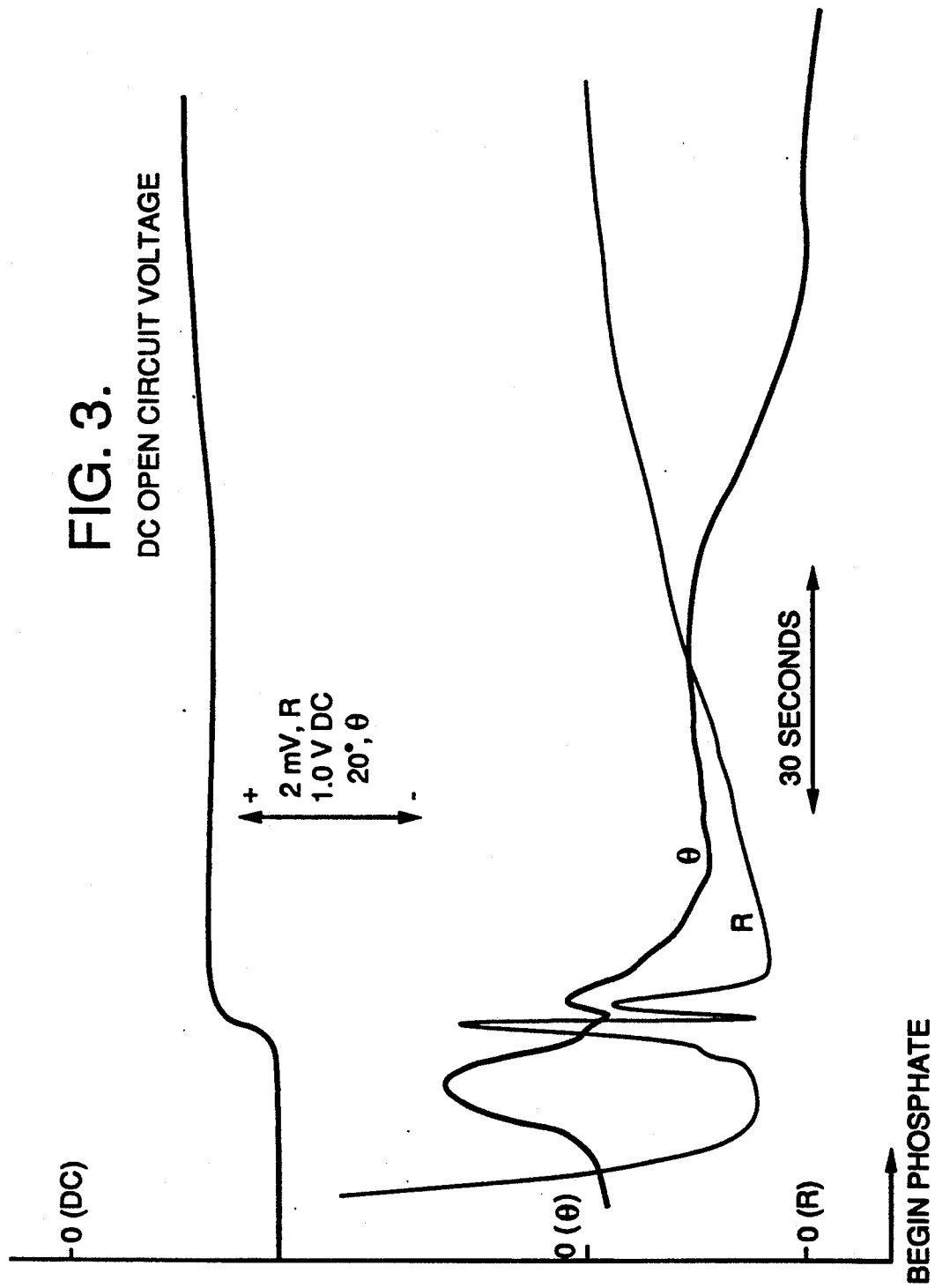

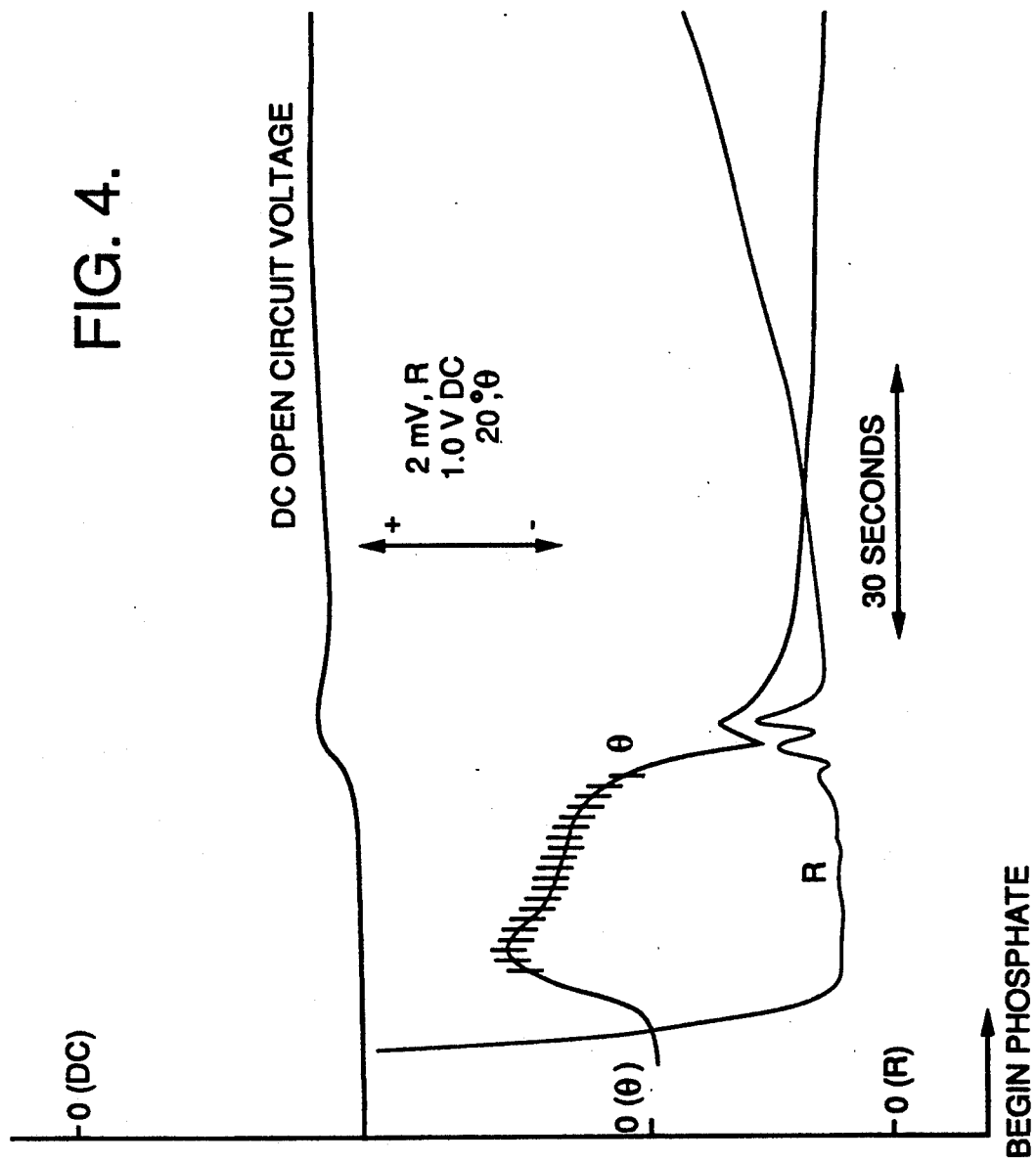

METHOD AND SYSTEM FOR MONITORING QUALITY OF PHOSPHATE COATING

BACKGROUND OF THE INVENTION

1. Field of the Invention

The present invention relates generally to the phosphating of metal surfaces having large areas wherein a layer of insoluble metal phosphate crystals is applied to the metal surface. More particularly, the present invention involves a non-intrusive method for monitoring and measuring the quality of such phosphate coatings during the phosphating process.

2. Description of Related Art

The treatment of metal surfaces to provide a coating of insoluble metal phosphate crystals is known as phosphating. The phosphate crystals strongly adhere to the metal surface and provide corrosion resistance and protection. Phosphate coatings are commonly used on metals as an excellent base for lacquer and paint finishes. Phosphating is commonly used in the automotive and appliance industries to provide both a paint base and corrosion resistance to metal surfaces prior to painting. Phosphating has also been used commonly in a wide variety of other industries to protect zinc, aluminum, cadmium, magnesium and their alloys.

The phosphating process usually involves dipping the metal surface into a tank containing a phosphating solution. Phosphating processes based on spraying the metal surface with phosphating solution are also commonly used. In order for the phosphate coating to provide desired corrosion resistance, it is important that the entire metal surface be covered with a uniform and unbroken layer of phosphate. Further, it is important that the quality of the phosphate coating be such that the phosphate crystals strongly adhere to the base metal and also provide a suitable surface finish to which lacquers and paints will bond.

Monitoring the quality of the phosphate coating presents many problems. These problems become especially critical when large metallic surfaces, such as car bodies and appliances, are inspected for the quality of phosphate coating. Phosphate quality is frequently not uniform over large manufactured metal surfaces. This lack of uniformity can be caused by many factors unrelated to the chemistry of the phosphate bath. Some of these factors are: non-uniform surface properties of the metal itself, non-uniform retention of drawing compounds over formed metal bodies, oil seepages from welded seams, non-uniform removal of heat scale, non-uniform cleaning of the metal, etc.

Because of the diverse causes and localized nature of problems associated with coating quality, the quality of the coating cannot be assessed by sample coupons. Non-destructive on-line quality monitoring is desirable. However, non-destructive methods such as X-ray fluorescence used on-line do not monitor the entire metal body and cannot therefore identify the location of smaller, localized quality defects on large surfaces.

Three important physical criteria of phosphate quality are coating weight, coating crystal size (or the relationship of crystal size and porosity) and coating composition (as exemplified in the technical literature by p-ratio). It would be desirable to provide a method and system for accurately monitoring the quality of phosphate coatings of large, complex industrial metal shapes and connected parts which is on-line, can detect and identify the location of localized defects as well as overall quality, and can measure coating weight, coating porosity or crystal size, and coating composition. Such an on-line monitoring method would eliminate many of the disadvantages associated with the present techniques.

SUMMARY OF THE INVENTION

In accordance with the present invention, a method and system are provided for monitoring the quality of the coating produced during phosphating of a metal substrate. The method and system are well-suited for monitoring the quality of phosphate coatings applied to large metal surfaces such as automobile bodies and appliances wherein variations in coating quality and coverage are difficult to detect.

The present invention is based on the discovery that the voltametric response between a large metal surface being phosphated and a large counter-electrode can be localized by judicious placements of reference electrodes. The reference electrode measurements provide valuable information regarding the quality of the phosphate coating on the metal surface.

The method of the present invention involves applying a selected dc current or potential between a metal substrate having a large surface area and a counter electrode while the substrate is exposed to a phosphating solution. A constant ac signal is superimposed on the dc potential or current. The resulting ac potential is then measured between the metal substrate and a reference electrode which is positioned in contact with the phosphating solution and located between the counter electrode and substrate. The resulting measurement of an ac potential provides a spectra that is an indication of defects in the phosphate coating applied on the metal substrate even when such defects are located within a relatively small region of the large surface area of the metal substrate.

In accordance with one embodiment of the present invention the counter electrode is large and surrounds the metal substrate on at least two sides and is relatively distant from the substrate.

In accordance with a second embodiment of the present invention, the counter electrode has a relatively small surface area compared to the metal substrate and is located in close proximity to the substrate. In this embodiment, the location of the defect in the phosphate coating on the substrate in relation to the counter electrode is determined from the ac spectra obtained.

In a third embodiment of the present invention, multiple counter electrodes are positioned in contact with the phosphating solution at selected locations in proximity to selected corresponding locations on the substrate. The ac potential is measured between each counter electrode and the corresponding location on the substrate to provide multiple ac spectra. Each spectra provides an indication of the quality of the phosphate coating on the metal substrate in proximity to each counter electrode. Thus, variations in the quality and homogeneity of the phosphate coating across the large surface area of the substrate are detected and attributed to a particular location on that surface area.

As a feature of the present invention, the use of dc voltammetry in conjunction with ac impedance spectroscopy to continually monitor phosphate coating quality provides an extremely reliable real time technique for determining phosphate coating quality during the phosphating process.

Another feature of the present invention is the use of combinations of counter and reference electrode sizes and locations to be able to localize defects on large metal surfaces.

The above-discussed and many other features and attendant advantages of the present invention will become apparent as the invention becomes better understood by reference to the following detailed description when considered in conjunction with the accompanying drawings.

DESCRIPTION OF THE DRAWINGS

FIG. 1a is an end view of a portion of a phosphating tank in which a preferred exemplary electrode system is depicted for monitoring phosphate coating quality on a truck body by ac impedance spectra in accordance with the present invention.

FIG. 1b is a partial side view showing a portion of the electrode array depicted in FIG. 1a.

FIG. 1c is an end view of a portion of a phosphating tank in which an alternate preferred exemplary electrode system is depicted for monitoring phosphate coating quality on a truck body by ac impedance spectra in accordance with the present invention.

FIGS. 2-10 show exemplary ac current spectra obtained in accordance with the present invention.

DESCRIPTION OF THE PREFERRED EMBODIMENTS

The present invention is useful for monitoring the quality of phosphate coatings which are applied during the phosphating process. Phosphating of metal surfaces is a well-known process which is described in detail in Kirk-Othmer's Encyclopedia of Chemical Technology (third edition, pages 304-308) and in Phosphating and Metal Pretreatment—A Guide to Modern Process and Practice by D. B. Freeman (Industrial Press, Inc., 1986). These two references and the references referred to hereinafter are hereby incorporated by reference.

In accordance with some, but not all, of the embodiments of the present invention, an ac impedance spectra technique is used which is similar to the basic process disclosed in U.S. Pat. No. 4,631,116, assigned to the present assignee. In that patent, a method is described for using dc voltammetry plus superimposed ac signals to yield ac impedance spectra to monitor the quality of plating bath solutions. The ac impedance spectra generated between a working electrode and a reference electrode was found to provide ac current spectra or fingerprints which were indicative of plating bath constituents.

Figure 1:
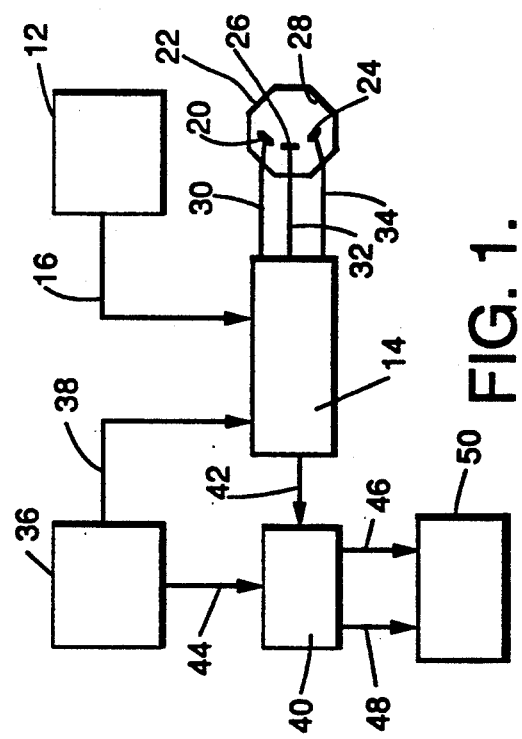
FIG. 1 is a schematic representation of the general system used in practicing the present invention.

A schematic diagram of an exemplary system for use in accordance with the present invention is shown in FIG. 1. The system includes a dc function or waveform generator 12 which is a conventional piece of equipment designed to provide a constant or slowly varying dc voltage.

The dc generator 12 should be capable of providing both constant and controlled slow variation of the dc voltage. Slow variation of the dc current or voltage is preferably provided by sawtooth waves having a frequency of up to 0.2 Hz with 0.03 Hz being preferred. (This low frequency ac current or voltage is referred to herein as dc.) The peak-to-peak voltages for such waveforms is preferably in the range of 40 mv to 600 mv. The use of a sawtooth waveform having a frequency of 0.03 Hz and a 300 mv peak-to-peak potential was found to be especially useful at the end of the phosphating time since the high impedance of the phosphate coating results in maximum currents of only about 600 microamps $cm^2$. The sawtooth wave is applied $\pm 150$ mv over a bias potential set at the mixed potential of steel of $-0.57$ V vs. saturated calomel electrode (SCE). Galvanize is set to the same bias potential.

The dc output from the dc function generator 12 is input into a potentiostat 14 as represented by line 16. In addition, a small ac signal from signal generator 36 is also input into potentiostat 14 as represented by line 38. The potentiostat 14 is a conventional potentiostat which has the function of insuring that the potential input from the ac signal generator 36 and from the dc function generator 12 is applied at the phosphating metal surface 20 uninfluenced by potential changes at the counter electrode(s) 24.

The potentiostat may be used in either the galvanostatic (controlled current) or potentiostatic (controlled potential) mode. The potentiostatic mode is preferred for ac superposed on sawtooth dc waves; the galvanostatic mode for large surfaces such as autobodies, for which the dc bias voltage from the dc generator 12 is set to 0.0 volts in order to provide zero dc current, thereby significantly lowering the cost of the power supply. In addition, the absence of dc current insures non-interference of measurements on the phosphating process itself.

When using dc sawtooth voltammetry with a superimposed ac signal, the generated spectra is always an ac current at a single ac frequency measured against the time during which the metal surface is undergoing surface variations based on the nature of the increasing build-up of phosphate coating. When using zero-dc current galvanostatic response the generated ac response can be of two types:

a) ac voltage as a function of ac frequency over a short time interval chosen during a particular time during the phosphating process; and b) ac voltage as a function of phosphating time at a particular frequency chosen between limits of about 10 Hz to 10,000 Hz.

Adjacent to surface 20 in the phosphating tank 22 is one or more counter electrode(s) 24 and one or more saturated calomel electrode(s) (SCE) or other reference electrode 26. The reference electrodes should be located between the substrate and the counter electrodes. Any metal wire or surface which exhibits a stable rest potential in the phosphate solution may be used as the reference electrode. Examples are stainless steel, copper, tinned copper, or platinum. For large surfaces, it is preferred that at least two relatively large counter-electrodes 24 be used and that numerous reference electrodes 26 be used. The surface 20, counter electrode(s) 24 and reference electrode(s) 26 are all immersed in the phosphating solution 28 so that there is a continuity of electrolyte solution between all three.

The present method is preferably used in dip tanks; however, the present method is amenable to phosphating systems which supply the phosphating solution by other means that can provide a continuity of an electrolyte solution path between the electrodes 24 and 26 and the surface 20. The locations of the counter electrodes 24 and reference electrodes 26 relative to the surface 20 may be varied to achieve localized measurements of coating quality. On large relatively complex surfaces, such as automobile or truck bodies, one or more counter electrodes and many reference electrodes are placed at various locations on the inside and/or outside of the automobile body.

The surface 20 and electrodes 24 and 26 are connected to the potentiostat 14 as represented by lines 30, 34 and 32 respectively. The potentiostat 14 provides galvanostatic and/or potentiostatic control of the ac and dc current or potentials applied between the surface 20 and electrodes 24.

The ac signal generator 36 is a conventional ac signal or waveform generator 36 which is capable of providing a small ac signal which is input into the potentiostat 14 as represented by line 38. The potentiostat 14 is designed to superimpose the small ac signal onto the dc signal or bias so that the dc bias applied between the surface 20 and counter electrode(s) 24 includes a superimposed ac signal. Both the ac current/potential and dc current/potential are measured by the potentiostat 14 and transmitted to a lock-in amplifier 40 as represented by line 42.

The lock-in amplifier 40 is of conventional design and is provided to selectively augment the response to the ac signal which is applied to the surface 20. A reference signal from the ac signal generator 36 is transmitted to the lock-in amplifier 40 as represented by line 44 so that the lock-in amplifier 40 may respond to the chosen ac signal frequency. In the galvanostatic mode, the output from the lock-in amplifier 40 is a measure of the ac potential between the surface 20 and a particular reference electrode 26 during the phosphating process. In the potentiostatic mode, the output from the lock-in amplifier 40 is a measure of the ac current between the surface 20 and a particular reference electrode 26.

As is conventionally known, typical lock-in amplifiers provide outputs measured in cartesian or polar coordinates which are referred to a chosen reference phase angle. These outputs are recorded by a recorder 50, such as a strip chart recorder, which is connected to the lock-in amplifier 40 as represented by the two lines 46 and 48.

The ac potential measurements from the lock-in amplifier 40 are input into a strip chart recorder 50 to provide the ac current/potential spectra. FIGS. 2-10 represent ac potential spectra wherein the potentiostat 14 was operated in the galvanostatic mode. The ac potential spectra is a plot of the ac potential versus the phosphating time. The details of the parameters and conditions under which the spectra in FIGS. 2-10 were generated are set forth in the examples below.

The ac signal in the galvanostatic mode preferably has a current which is about 4 microamperes per square centimeters, but it has no upper limit. In the potentiostatic mode the peak-to-peak potential of the ac signal is preferably equal to or below about 25 mv. The preferred ac signal frequencies are between about 10 Hz to 10,000 Hz.

The types of surfaces which may be monitored during phosphate coating include any of the metal surfaces which are amenable to phosphate coating. These surfaces include steel, aluminum, iron and their alloys. The size and shape of the surface is not critical.

In accordance with the present invention, the surfaces are monitored for the presence of defects in the phosphate coating. A defect is considered to be an area of unacceptable quality due to unacceptable coating weight or porosity. The method is especially well-suited for detecting the presence of defects and their location on the surface being monitored.

For large stationary surfaces, it is preferred that more than one counter-electrode be placed at strategic locations. Alternatively, one or two counter-electrodes are used with many reference electrodes placed at strategic locations. For continuous conveyor belt phosphating procedures, it is possible to place counter electrodes at spaced locations to monitor the phosphate coating quality as the metal surface passes along and through the phosphating tank. Such continuous systems are conventionally employed for phosphating automobile bodies and other items having large surface areas and high volume production rates, such as appliances.

In continuous systems where the surface being phosphated is moved through the tank and past the electrodes, the procedure of placing separate counter-electrodes close to those localized areas whose quality is to be monitored is straightforward. For example, a multiplexer can be used to rapidly switch to all counter-electrodes next to the moving metal surface to give a "snapshot" at one short interval in time, to repeat at later intervals with counter-electrodes "down-line" in the tank, and then use a computerized data acquisition system to sort the appropriate "snapshots" to give an ac signal response of each individualized section of the large metal surface as a function of time in the phosphating solution.

Figure 1B:
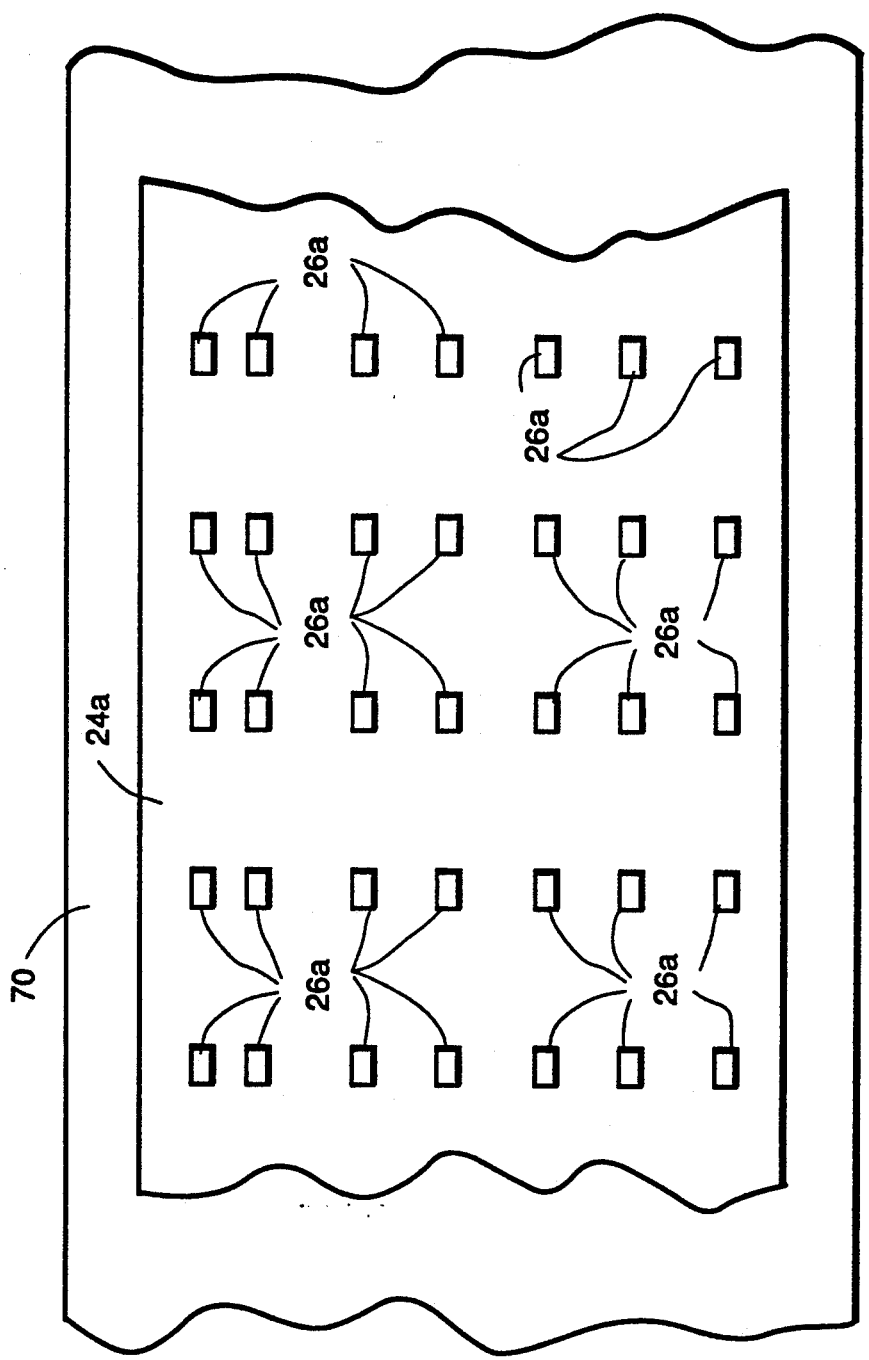
Figure 1D:
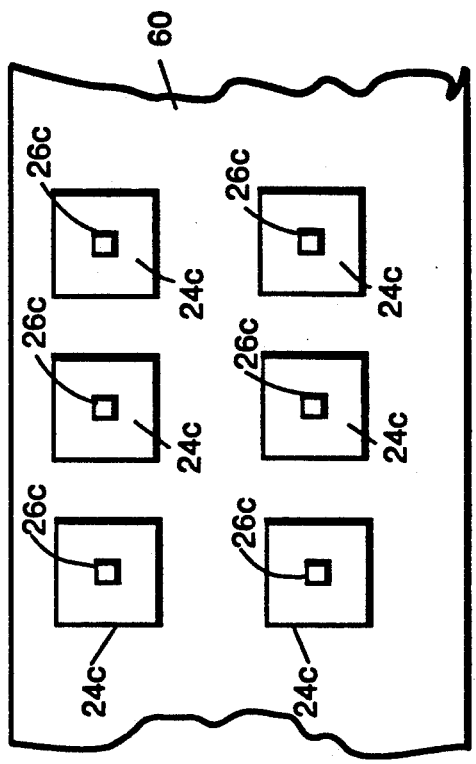
FIG. 1d a side view showing a portion of the electrode array depicted in FIG. 1c.

FIGS. 1c and 1d are partial diagrammatic representations of a system for monitoring the quality of a phosphate coating being applied to a truck body 60. The truck body 60 is shown being immersed in a phosphating tank 62 which contains conventional phosphating solution 64. A number of counter-electrodes 24c are placed at localized areas surrounding the truck body 60. Reference electrodes 26c are located around the truck body 60 at selected locations in the proximity of the various truck body surfaces and between the counter-electrodes 24c and the truck body 60. The potential is applied to the truck body 60 via line 30. Details of the various connections of the counter-electrodes, reference electrodes and truck body to the potentiostat and related monitoring equipment as shown in FIG. 1 are not shown in FIGS. 1c and 1d.

An alternate preferred embodiment is to place one or two large continuous counter-electrodes or multiplexed sets thereof, into the phosphating tank so that they are in the vicinity of all localized sections to be monitored at all times that phosphating is occurring. A large number of reference electrodes are individually placed between the counter-electrode and the large metal surface being phosphated. Measurements of the potential at the various reference electrodes are multiplexed as described above.

FIGS. 1a and 1b show a partially diagrammatic representation of the above-described alternate preferred exemplary embodiment wherein a truck body 70 is placed within a phosphating tank 22a which contains conventional phosphating solution 74. This system includes two large counter-electrodes 24a which are connected to the potentiostat and related monitoring equipment (not shown) by line 32a. When using such large counter-electrodes, it is preferred that an insulating layer 66 be provided between the counter-electrodes 24a and the phosphating tank walls. Reference electrodes 26a are placed in the proximity of the truck body at selected locations to provide localized monitoring capability. The potential or current is applied to the truck body via line 30a. The potentiostat, and related monitoring equipment, including a multiplexer, are connected to the large counter-electrodes 24a, reference electrodes 26a and truck body 70 via lines 30a, 32a and 34a. For simplicity, the monitoring equipment, which is conventional in nature and diagrammed in FIG. 1 is not shown in FIGS. 1a or 1b. Also, for simplicity, the multiplexer interrupts between line 34a and individual reference electrodes 26a are not shown. Likewise the interrupts between 32a and 24a are not shown.

The use of large counter-electrodes provides two advantages: the reference electrode circuits are very high impedance and it is simpler to switch voltage signals than current-carrying signals; but most importantly, a large, current-carrying counter-electrode tends to focus local currents and thereby make the reference electrode readings more localized. Currents from numerous smaller counter-electrodes will tend to delocalize to lower impedance defects on the metal surface, and therefore give less localized quality information.

The extent of dc bias or variation, if any, is determined experimentally to obtain the ac spectra with the most detail or information. When large surfaces are monitored by the method of the present invention, it is preferred to use zero dc bias to reduce the large dc current required to cathodically or anodically bias the surface.

Examples of practice are listed below. The examples show that diagnostic ac spectra can be obtained that relate to key quality aspects of phosphate coatings. By locating a large counter electrode away from the surface being phosphated and locating the reference electrodes closer to a metal substrate, defects as small as 5% of the substrate area can be not only detected, but also localized. Furthermore, using the same counter electrode/reference electrode configuration, diagnostic spectra can be obtained on complex shaped parts. Alternatively, by positioning a relatively small sized counter electrode close to the substrate surface, the location of a small sized defect can be determined. However, in this case many counter-electrodes need to be individually connected and disconnected.

The system shown schematically in FIG. 1 was used to determine phosphate quality of various sized and shaped metal surfaces using a commercially available phosphate process presently employed in the automotive industry. The Parker Amchem Bonderite 958 Phosphate Process was used. A typical process cycle consisted of the following individual process steps:

1) Parco Cleaner 1500, (obtained from Parker Amchem of Madison Heights, Mich., a division of Henkel Corporation) 2 minutes
2) Slightly alkaline water rinse, 45 seconds
3) Fixodine Z-8 Conditioner (obtained from Parker Amchem), 1 minute
4) Bonderite 958 phosphating solution (obtained from Parker Amchem), with Additives 319, 301, 302, Primer 40 and accelerator 130.
5) Deionized water rinse.
6) Blow dry the sample surface with air.

If deemed necessary for the performance of a particular test, a specific process step was omitted. With regard to the preparation, operation, and maintenance of the individual process solutions, instructions in the Parker Amchem Technical Process Bulletins were followed.

Substrate materials used in these examples were cold-rolled steel, hot-dip galvanize, and electrogalvanize. Substrate shapes were either flat sheet or a complex shape which consisted of a simulated automobile door with exterior and interior surfaces. The interior surfaces were accessible to phosphating solution through drainage holes.

EXAMPLE 1

The ac spectra shown in FIGS. 2–6 demonstrate the capability of the method of the present invention to be responsive to three important phosphate coating quality parameters: (1) nonuniformity in the phosphate coating due to localized surface contamination; (2) coating weight; and (3) crystal size. The spectra shown in FIGS. 2–6 were obtained on one inch x one inch (2.54 cm $\times$ 2.54 cm) hot-dip galvanize substrate material. The system used a large counter electrode (effective area greater than 10 $in^2$ or 64.5 $cm^2$), located 3 in. (7.6 cm) from the galvanize. The reference electrode was located $\frac{3}{8}$ (0.75 cm) out into the solution from the center of the substrate galvanize surface. The applied signal was 3.9 rms $\mu A/cm^2$, 100 Hz.

Figure 5:
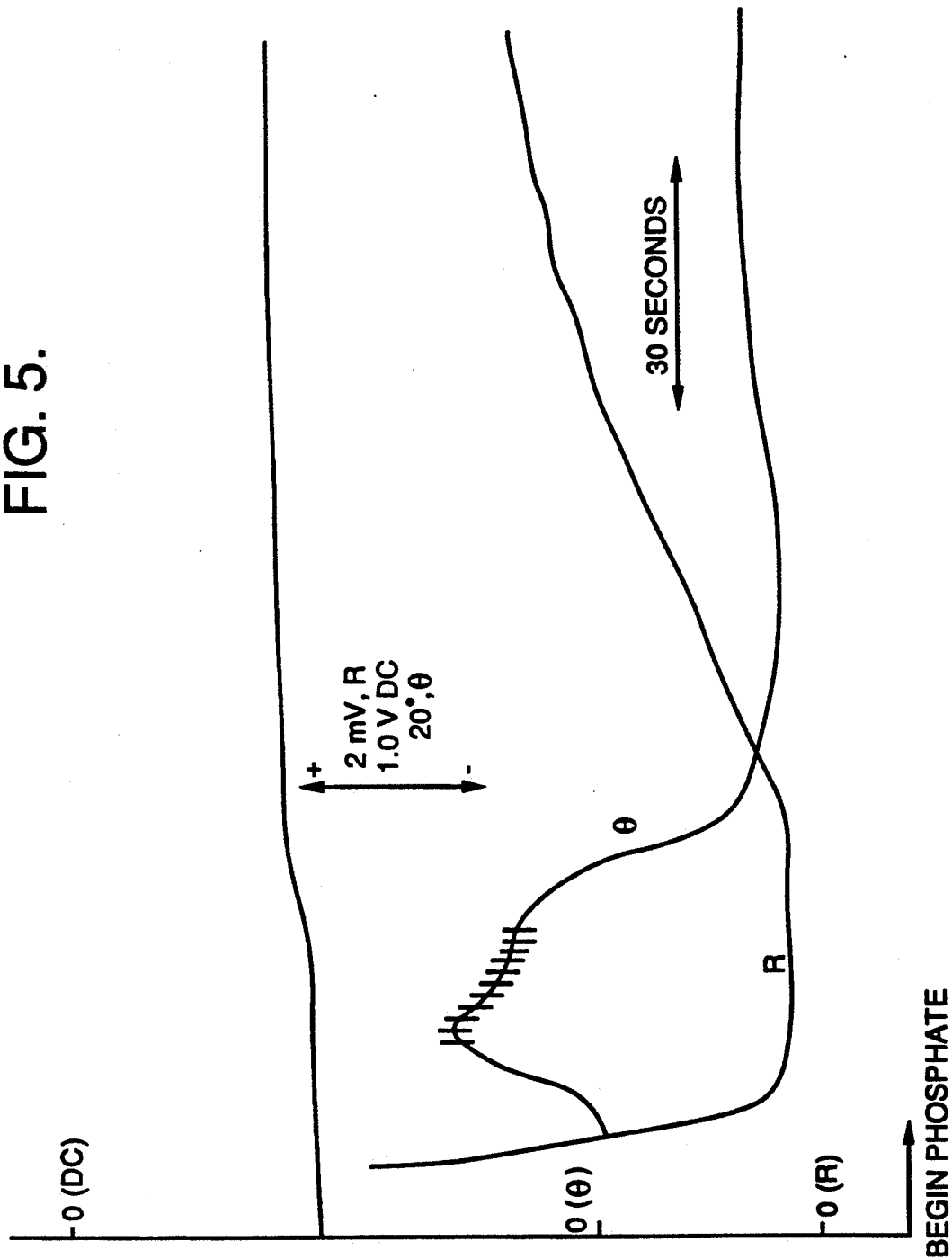
Figure 6:
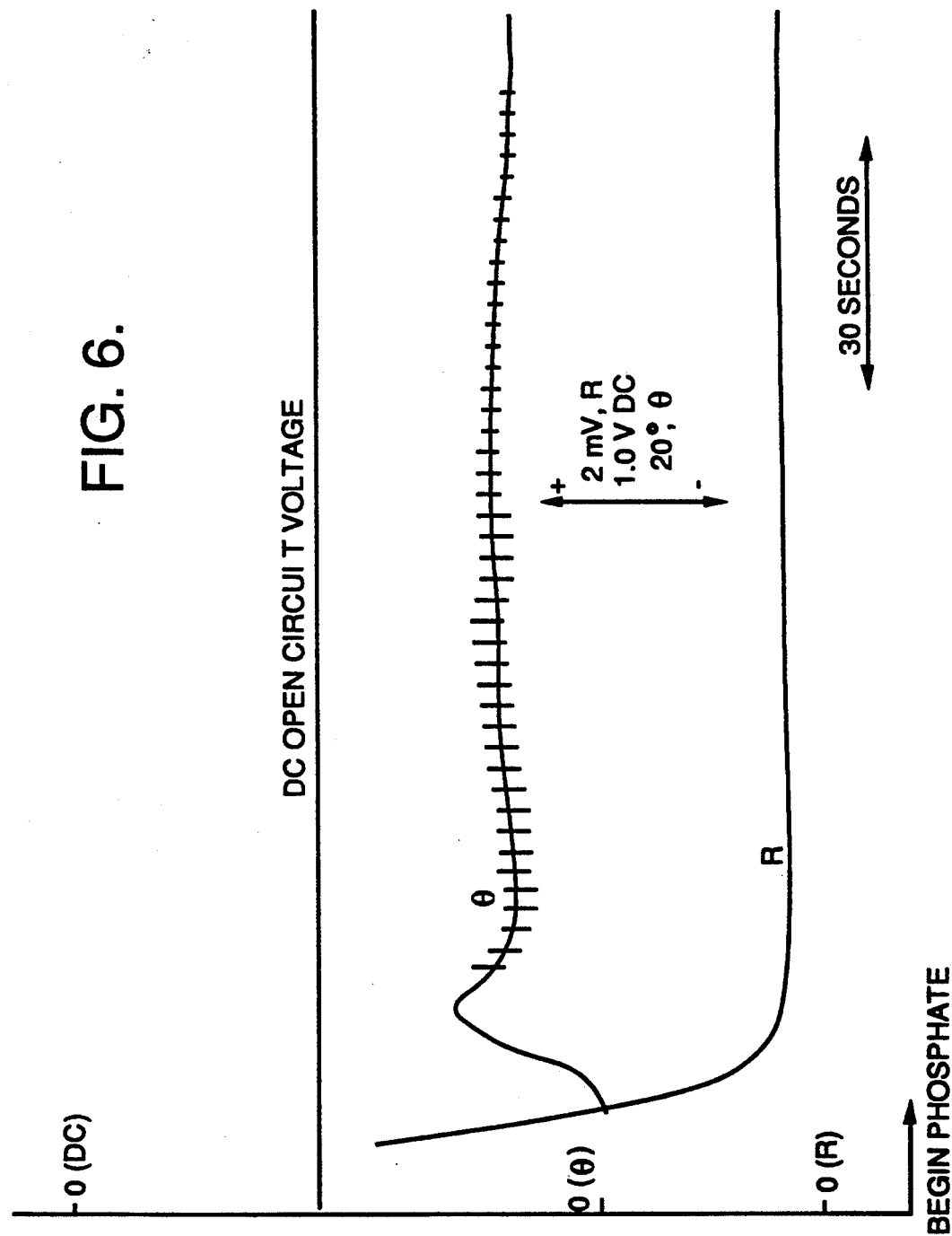

In these examples, substrate surface contamination was simulated by coating 0.05 $in^2$ (0.008 $cm^2$) at the center of the metal substrate with a thin film of Quaker Ferrocote 61 AUS oil, which was subsequently wiped to leave just a trace of oil. Variations in crystal size and coating weight were effected by changing the amount of time the substrate material was allowed to remain in the conditioner. No cleaner prior to the conditioner was used. The variations in oil coverage and use of or bypass of the conditioner bath for the six substrates shown in FIGS. 2–6 are summarized in Table 1. FIG. 2 shows the spectra obtained with and without (w/o) conditioner when no oil coating was applied. FIG. 3 shows the spectra obtained with 5% of the 1 inch square surface oiled, and with 60 seconds in the conditioning bath. The conditions in FIG. 4 were the same as FIG. 3 except the conditioning bath was bypassed. In FIG. 5, 100% of the metal surface was coated with the oil, and the metal coupon was immersed in the conditioner bath for sixty seconds. The spectra in FIG. 6 represents a condition of virtually no coating because both inhibitions, 100% oil and absence of conditioning, were present.

TABLE 1

| | VARIATIONS IN OIL COVERAGE AND CONDITIONER TIME | |
|---|---|---|
| Figure | Ferrocote Oil (% of Area) | Conditioner Time (seconds) |
| 2 | 0 | 60 |
| 2 | 0 | 0 |
| 3 | 5 | 60 |
| 4 | 5 | 0 |
| 5 | 100 | 60 |
| 6 | 100 | 0 |

It is well known that the purpose of the initial conditioning process step is to produce the desired coating morphology, which consists of small sized crystals. The production of small sized phosphate crystals leads to rapid coverage of the substrate metal with a thin, low porosity phosphate coating. A thin coating is one which has a small coating weight. Omission of the conditioning step results in the formation of large phosphate crystals. Large crystal morphology leads to a thicker, more porous, and heavier coating. Scanning electron micrographs of the phosphate coating morphology from the experiments represented by FIGS. 2, 3 and 4 with and without conditioner and with and without 5% oil are shown in Table 2. Oil and the absence of conditioner result in more porous, large crystal coatings, which correlate with decreased phase angle and decreased magnitude of ac signal.

TABLE 2

EFFECTS ON MORPHOLOGY OF COATING

| Test Condition | Average Crystal Size (micrometers) |
|---|---|
| With conditioner (no oil) | 6 |
| Without conditioner (no oil) | 13 |
| With oil (no conditioner) | 18 |

The diagnostic spectra shown in FIGS. 2–6 were obtained using the zero dc current method of the present invention. In this variant of the present method, the applied waveform is an alternating current superimposed onto a zero dc current bias, which is accomplished by using the potentiostat under galvanostatic control. Galvanostatic control is useful when dealing with galvanized substrates because the mixed potential changes significantly during the phosphating process. The measured response of this method is the magnitude (R) and phase angle ($\theta$) of the ac voltage with respect to a calomel reference electrode placed close to the substrate. Also included in FIG. 2–6 is the change in mixed potential of the substrate, measured with respect to the saturated calomel reference electrode. The voltage responses were obtained during the full period of immersion in the phosphate bath. The spectra were obtained in the first harmonic mode using a 100 Hz, 3.9 $\mu A/cm^2$ applied signal.

Without ascribing a specific theory or impedance model to the data shown in FIGS. 2–6, it is evident that unique impedance-time spectra were obtained for the six different process conditions given in Table 1. These process conditions represent variations in coating weight and uniformity of the phosphate coating. Generally, the spectra are characterized by an initial, or induction, period where the nucleation of the coating has not started and R and $\theta$ are close to zero. This is followed by a period of nucleation and growth of the phosphate coating, where R and $\theta$ are changing significantly. The final period is characterized by an approximately constant R and $\theta$, representing a steady state condition between deposition and dissolution of the phosphate coating. FIG. 2 shows that the effect of conditioner is to accelerate the nucleation and growth of the phosphate coating. Also, the final value of the phase angle is smaller for the case without conditioner.

When 5% of the substrate surface is covered with oil, it can be seen as shown in FIG. 3, that the impedance and phase angle decrease significantly. This is due to the fact that current continues to flow in the oiled region even after the formation of the high impedance coating on the remainder of the substrate. It should be noted that the metal under the oil film forms a phosphate layer. But, as indicated in Table 2, the morphology of the phosphate coating under the oil film consists of larger, irregularly shaped crystals. This implies that the coating has a higher porosity in this region. Comparing FIGS. 2 and 3 clearly demonstrates the sensitivity of the present method to small, inferior quality, non-uniformities in the phosphate coating.

EXAMPLE 2

Figure 7:
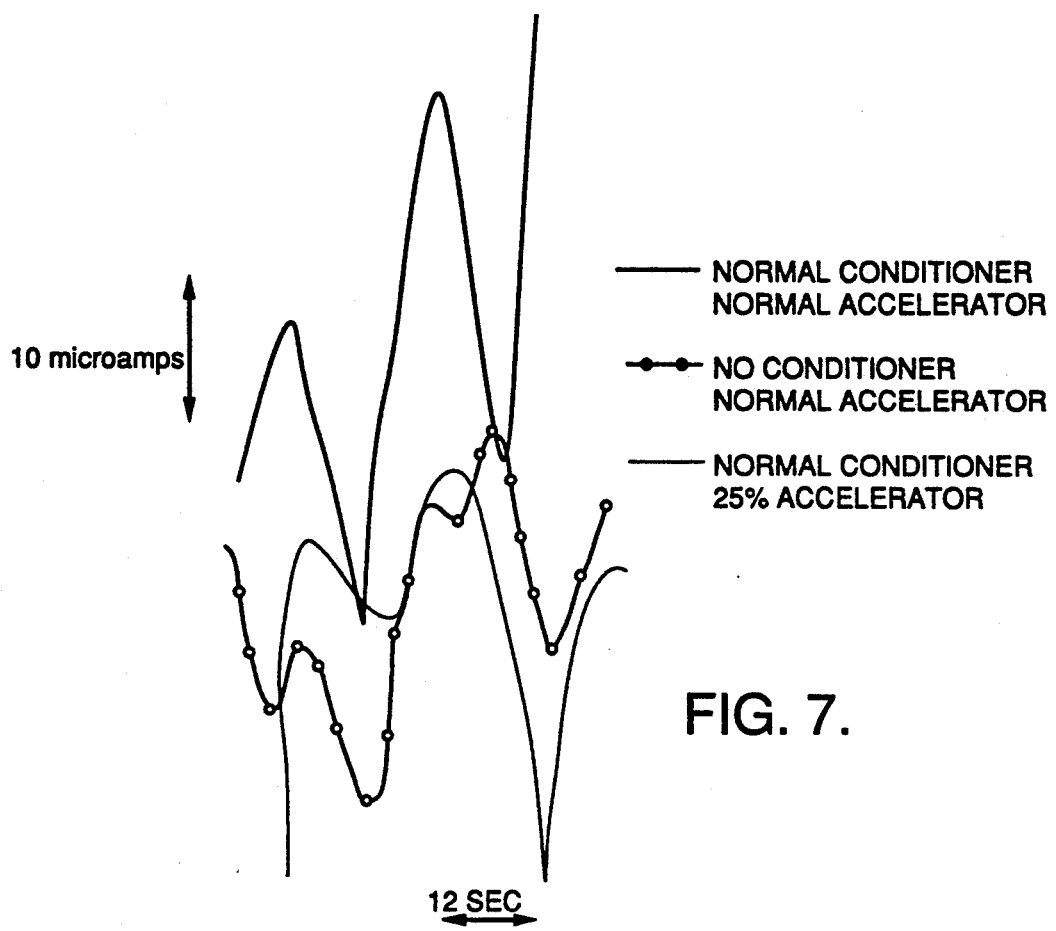
Figure 8:
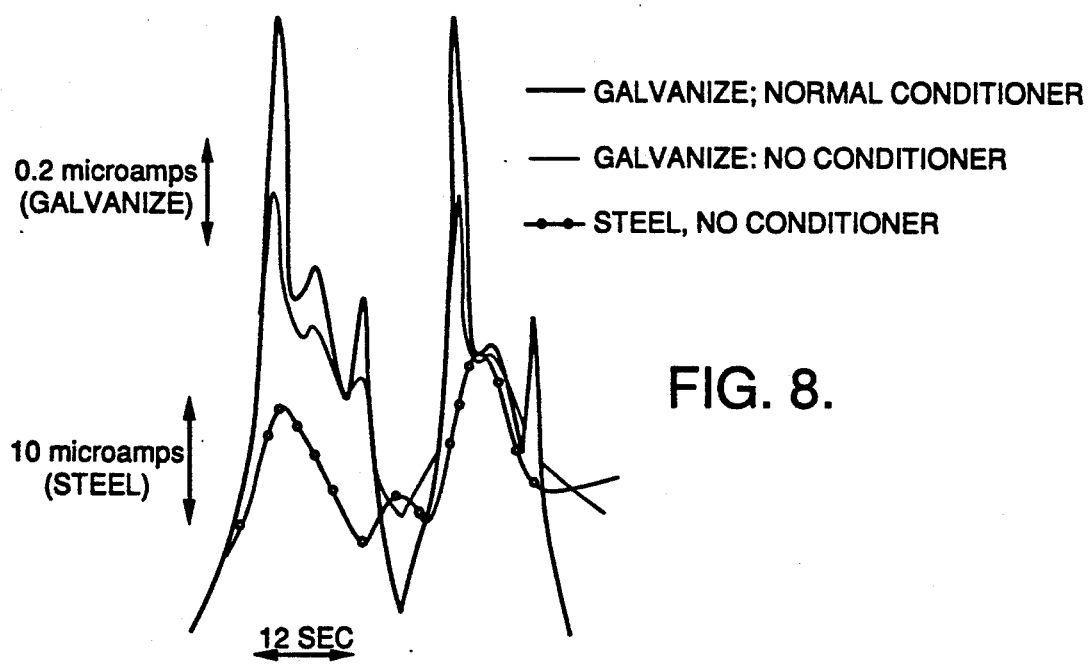

Utilization of a slowly varying dc voltage upon which a low amplitude ac voltage is superimposed in practicing the present invention yields distinct and diagnostic spectra under potentiostatic control compared to the zero dc current approach described in Example 1. Furthermore, additional refinement of the spectral details is obtained by measuring the second harmonic current response. To demonstrate the effectiveness of the slowly varying dc voltage approach, spectra were obtained under the following process conditions: (1) 60 seconds conditioning time, and 4 oz/gallon (30 gm/liter) accelerator; (2) omit the conditioner process step; and (3) reduce accelerator to 1 oz/gallon (7.5 gm/liter). As described above, the conditioner affects the crystal size and coating weight. The ac spectra were obtained on cold rolled steel. The 1 in.×1 in. (2.54 cm×2.54 cm) test samples were cleaned in Parco Cleaner 1500 for 2 minutes and alkaline rinsed for 45 seconds prior to conditioning and phosphating. The applied electrification waveform consisted of a 50 Hz, 25 mV rms ac voltage superimposed onto a low frequency continuous triangular wave. The triangular wave was swept at 20 mV/sec and extended 150 mV above and below a constant bias set at −0.57 V versus a saturated calomel electrode. The maximum current from the triangular wave was 2.9 $mA/cm^2$. Currents on the order of 3.0 milliamps per square centimeter or less are preferred. The quadrature component of the second harmonic ac current response was found to be diagnostic to conditioner. Segments of the ac spectra, taken after 1.5 minutes immersion in the phosphate bath, are shown in FIG. 7. Increasing the amount of the accelerator increases the magnitude of the peaks. The absence of conditioner decreases the magnitude of the peaks and results in additional peaks. It can be seen that highly diagnostic and multipeaked spectra indicate the effect of bath constituents on the nature of the phosphating process. The zero dc current approach does not yield responses with this type of multipeaked fine structure.

EXAMPLE 3

The multipeaked nature of the response to low frequency triangular "dc" (i.e. low frequency ac) voltage sweeps is also useful in determining the chemical composition of the formed phosphate coating. The ratio of zinc to iron in the phosphate coating is one method that is commonly used to evaluate coating quality. An indication of the response of this method to coating composition was obtained by comparing the spectra obtained from coatings formed on cold rolled steel and hot dip galvanize. For the Parker Amchem process used here, it is known that comparable coating weight and porosity are obtained on both substrates, although the formation time for the steel is longer. However, the coating on galvanize is less than 0.3% iron, while the iron content of the coating on the steel is 10%. Therefore, any difference in the ac spectra may be attributed to composition variations. The 500 Hz second harmonic, in-phase component of the spectra are shown for the steel and galvanize substrates in FIG. 8. The second harmonic, in-phase spectra were obtained with a 25 mV, 500 Hz sine wave superposed on a triangular wave set at −0.57 V bias, 150 mV at 20 mV/sec. The maximum triangular wave current was 78 $\mu A/cm^2$ after 3 minutes immersion of the galvanize and 100 $\mu A/cm^2$ after 6 minutes immersion for steel. The spectra were taken after the phosphate coatings were completely formed, which was three minutes for the galvanize and six minutes for the steel. Again, the reason for waiting until the end of phosphating was to highlight coating composition details over coating formation details. The iron content of the coating radically modifies the spectra.

EXAMPLE 4

In this example, a comparison is made between the spectra obtained on a flat substrate and a more complex shaped substrate. The principal feature of the complex shape is its internal structure, which allows access by the phosphating solution through a slot and two small holes. This shape simulates the complexity that would be found on an automobile door. Nominally, the dimensions of these mini-doors were 2.5 in.×2.5 in.×0.25 in (6.4 cm×6.4 cm×0.64 cm), and consisted of two parts that were spot welded together.

Figure 9:
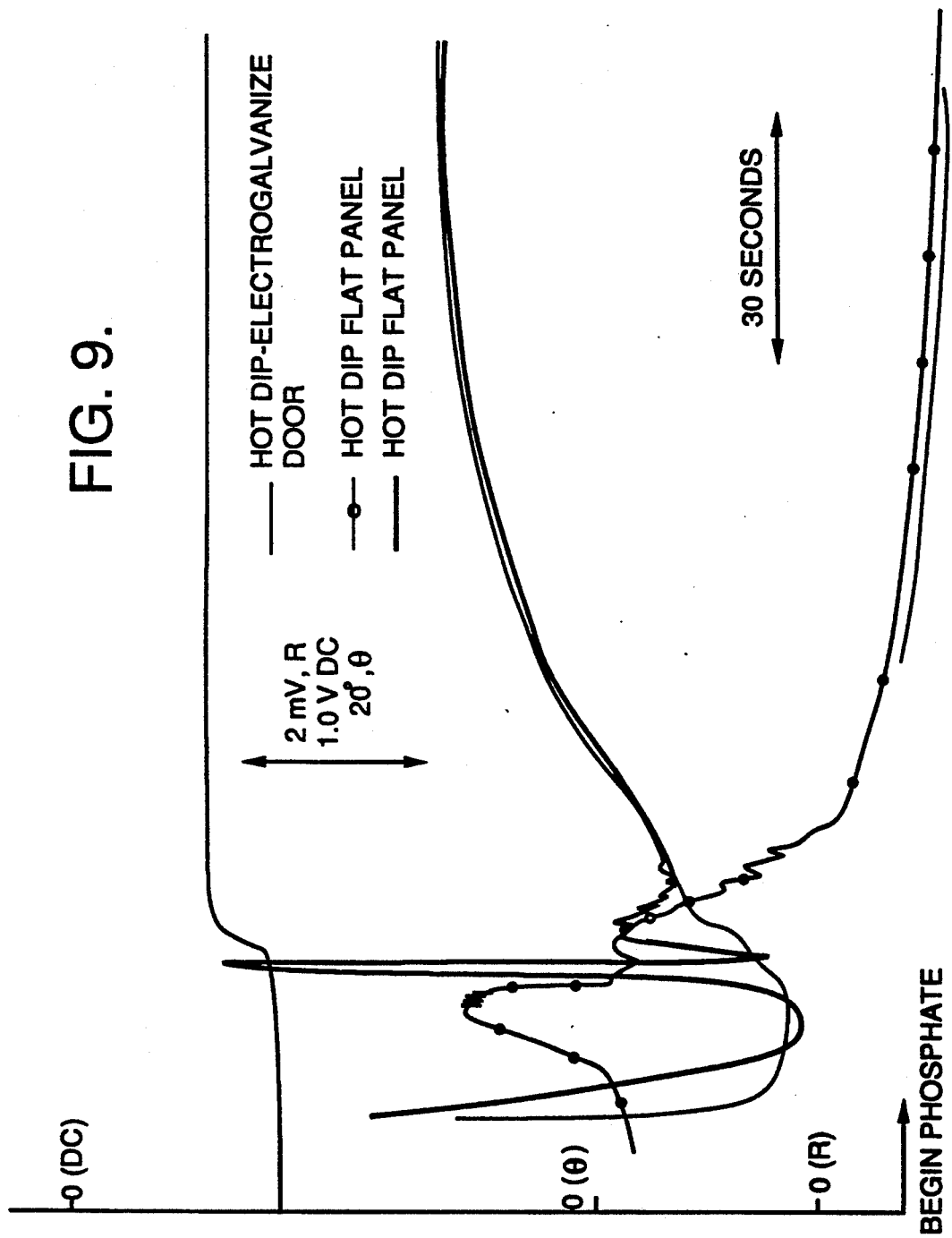
Figure 10:
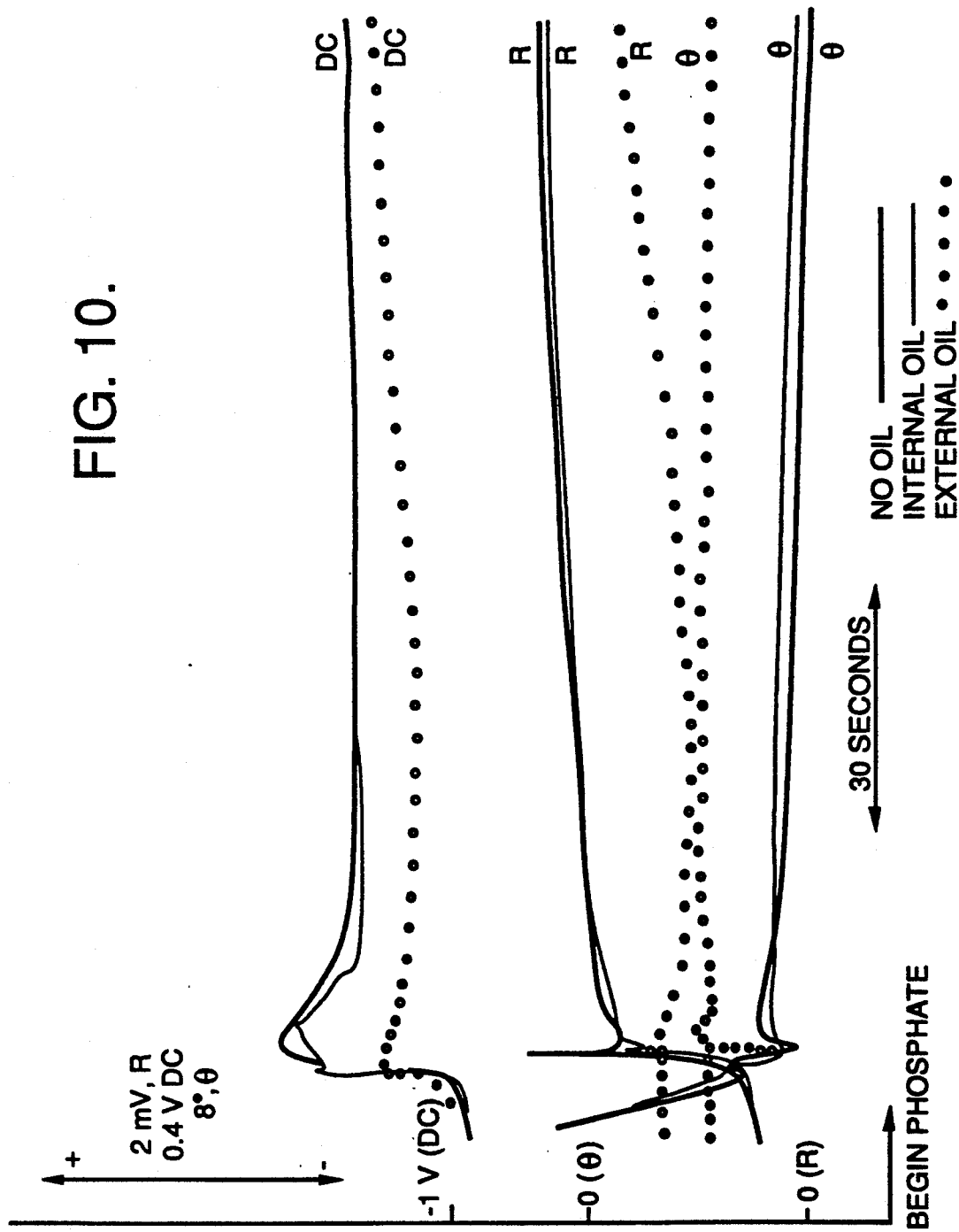

FIG. 9 shows the galvanostatically controlled ac spectra obtained for a mini-door and a flat sheet. The flat sheet was hot dip galvanize. One part of the mini-door was hot-dip galvanize and the other part was electrogalvanize material. The flat sheet was degreased but otherwise not cleaned prior to phosphating. The mini-door was cleaned with Parco Cleaner 1500 prior to the conditioner treatment. Both parts were processed in the conditioning bath for the same amount of time. The spectra were obtained using the zero dc current approach described in Example 1. The same current density was applied to both samples, namely, 3.9 $\mu A/cm^2$ rms at 100 Hz. All inside and outside areas were counted equally in calculating the total applied current for the complex shaped part. The counter electrode configuration was the same as in Example 1. The reference electrodes were also located in the solution at $\frac{3}{8}$ in. (0.75 cm) from the center of both shapes. It can be seen in FIG. 9 that the complex shaped part yields very similar spectra as that obtained for the flat material. The important discovery is that the rate of change and absolute values of R and $\theta$ are not affected by complex shapes, welds, or thin gaps in overlap areas, which would be features of many practical parts. Furthermore, the similarity in ac spectra demonstrates that the system configuration where the counter electrode surrounds the part allows the present method to be as sensitive to internal surfaces as it is to external areas. The only difference between the spectra for the flat substrate and for the mini-door is the absence of the spikes in the spectra for the mini-door. However, the spikes were not needed diagnostically, as shown in FIGS. 2 through 6. The spikes indicate the onset of nucleation and crystal growth on the substrate surface. For a substrate having a complex shape, it is reasonable to expect that the nucleation process does not occur at the same instant of time everywhere on the substrate.

EXAMPLE 5

The capability of the present method to determine the location of defective coating regions is now addressed. The response of the method depends on current flow. When the counter electrode is large and relatively far from the substrate, the current will flow to most regions of a complex shaped part. If the counter electrode is small and located very close to the part being evaluated, the flow of the current will be limited by the resistance of the phosphating solution. To demonstrate the effectiveness of a small counter-electrode configuration, the following three tests were performed. A small counter electrode, $\frac{1}{8}$ in.×3/16 in. (0.32 cm×0.48 cm), was placed 3/16 in. (0.48 cm) out into the solution from the center of the front surface of a mini-door which was described in Example 4. The reference electrode was placed halfway between the counter-electrode and the mini-door surface. A 100 Hz, zero current dc, 88 $\mu$amp ac current was used. On one door, a $\frac{1}{2}$ in.×$\frac{1}{2}$ in. (1.27 cm×1.27 cm) oil film was applied to the center of the front surface, under the counter electrode. On another door, a similar oil film was placed on an inside surface of a door. On the third door, no oil film was applied. The doors were cleaned prior to oil application, and placed into the conditioner after oiling. Oiling took 15 seconds between cleaning and conditioning. The results, shown in FIG. 10 indicate that external oil, but not internal oil was detected.

External defects can be differentiated from internal defects by proper placement of counter and reference electrodes and selection of size of counter electrodes. A large and distant counter electrode with a distant reference electrode locates both internal and external defects. A small close counter electrode with close reference electrode locates only external defects. In this way, two electrode configurations can be used in conjunction to differentiate between internal and external defects.

EXAMPLE 6

Figure 11:
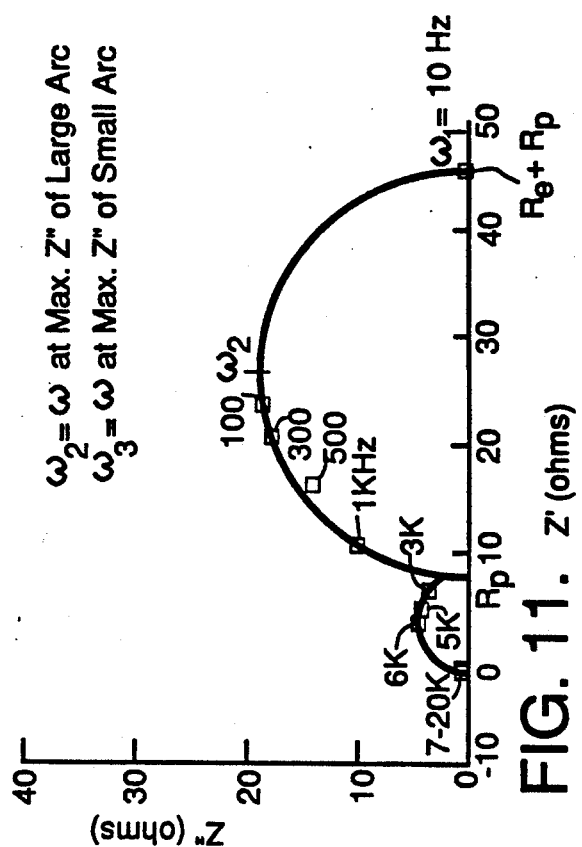

Instead of obtaining spectra of voltage as a function of phosphating time, ac voltage of a steady state, completed phosphate coating can be obtained as a function of frequency. A 1 in×1 in. (2.54 cm×2.54 cm) galvanize surface gave the spectrum shown in FIG. 11, which was obtained after 2 minutes of phosphating had taken place. A large, distant counter electrode was used with a close ($\frac{1}{8}$ in. or 0.32 cm distant) centrally located reference electrode to minimize solution resistance. A zero dc galvanostatically controlled 25 microamp ac signal was used. A model of the impedance of a phosphate coating led to equations that linked four parameters: capacity of a high quality, minimum porosity coating, $C_c$; capacity within a pore, $C_p$; resistance within a pore, $R_p$; and the electrical resistance, $R_e$, of reactions occurring at the metal interface at the base of a pore. Calculations indicate that $C_c << C_p$. Theory suggests that a frequency dispersion could be used to unequivocally determine the four parameters. If $\omega_1 < \omega_2 < \omega_3$, then at $\omega_1$, $R_e + R_p$ is determined; between $\omega_2$ and $\omega_3$, $R_p$ is determined; at $\omega_2$, $C_p$ is determined; and at $\omega_3$, $C_c$ is determined. Impedance measurements of Z' (in-phase impedance vector), Z" (quadrature vector) and frequency as parameter, are illustrated in FIG. 11.

Satisfactory results are obtained on a 1 in.×1 in. (2.54 cm×2.54 cm) phosphated surface: $R_p$=8 ohms, $R_e$=37 ohms, $C_c$=4 micro farads, $C_p$=160 micro farads. The two time constants are represented by the two semicircles. These values can be used to calculate coating thickness and porosity, as exemplified by the simplified relations, where:

T=thickness

P=fraction of coating area which is porous k=proportionality constant $\omega$=frequency $$P = k_2 C_p \quad (1)$$

$$T = k_3 R_p P \quad (2)$$

$$\omega_2 R_e C_p = 1 \quad (3)$$

$$\omega_3 R_p C_c = 1 \qquad (4)$$

As ascertained from FIG. 11, and $R_e$ $R_p$ are directly measured. $R_p$ is determined by extrapolation of measured data. Therefore $C_p$ and $C_c$ are determined by means of equations (3) and (4) above. These values are then substituted into equations (1) and (2). The constants $k_2$ and $k_3$ are determined by means of independent measurements of thickness and porosity.

The small circle in FIG. 11 is often difficult to obtain with sufficient accuracy. However, it is not required in equations (1) and (2). The large circle should always have a singular radius. The lower frequency part of the circle can be unequivocally obtained and the higher frequency part can then be extrapolated to accurately obtain $R_p$.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A method for monitoring the quality of a phosphate coating applied to a metal substrate having a large surface area, wherein said phosphate coating is applied by exposing said metal substrate to a phosphating solution, said method comprising the steps of:
   (a) applying a selected dc current or potential between said metal substrate and a counter electrode while said substrate is exposed to said phosphating solution;
   (b) superimposing a constant ac signal on said dc potential or current applied between said metal substrate and said counter electrode, said ac signal having a peak-to-peak potential or current, and a frequency;
   (c) providing said counter electrode positioned in contact with said phosphating solution;
   (d) providing at least one reference electrode positioned in contact with said phosphating solution and in proximity to said substrate, wherein said reference electrode is located between said counter electrode and said substrate;
   (e) measuring the ac potential between said metal substrate and said reference electrode, said measurement of ac potential being expressed as an ac spectra which provides a continual, real-time indication of defects in the phosphate coating applied to said metal substrate wherein said defects are located within a small region of said large surface area of said metal substrate.

2. A method for monitoring the quality of a phosphate coating according to claim wherein said counter electrode surrounds said metal substrate on at least two sides and is distant from said metal substrates 3. A method for monitoring the quality of a phosphate coating according to claim 1 wherein said counter electrode has a relatively small surface area compared to said metal substrate and is located in close proximity to said metal substrate whereby the location of said defect in relation to said counter electrode is determined.

4. A method for monitoring the quality of a phosphate coating according to claim 3 wherein said metal substrate comprises a complex structure having two opposing metal structures with an air gap therebetween, each metal structure having an inner surface adjacent to said air gap and an outer surface, and wherein said counter electrode is positioned in close proximity to said outer surface of one said metal surface whereby said defects present only on said outer surface of said one metal structure are determined.

5. A method for monitoring the quality of a phosphate coating according to claim 1 wherein:
   (a) said counter electrode has a large surface area;
   (b) multiple reference electrodes of small surface area are provided in close proximity to said substrate and uniformly dispersed over said large surface area of said substrate, whereby the location of said defects on said substrate in relation to one of said reference electrodes is determined.

6. A method for monitoring the quality of a phosphate coating according to claim 5 wherein said dc potential is varied between about 40 millivolts to 600 millivolts peak-to-peak at a frequency of less than about 0.2 hertz.

7. A method for monitoring the quality of a phosphate coating according to claim 1 further comprising:
   providing multiple counter and reference electrodes positioned in contact with said phosphating solution and at selected locations in proximity to selected corresponding locations on said metal substrate; and performing said measuring of step (e) between each of said reference electrodes and said selected corresponding location on said metal substrate to provide multiple ac spectra wherein each said ac spectra provides an indication of the quality of the phosphate coating applied to said metal substrate in proximity to each of said counter electrodes whereby variations in the quality and homogeneity of said phosphate coating across said large surface area of said metal substrate are detected and attributed to a particular location on said large surface area of said metal substrate.

8. A method for monitoring the quality of a phosphate coating according to claim 1 wherein said selected dc potential or current is varied.

9. A method for monitoring the quality of a phosphate coating according to claim 1 wherein the density of the current of said dc signal is less than or equal to about 3.0 milliamps per square centimeter.

10. A method for monitoring the quality of a phosphate coating according to claim 1 wherein the frequency of said ac signal is between about 10 Hz to 10,000 Hz.

11. A method for monitoring the quality of a phosphate coating according to claim wherein said metal surface is immersed in said phosphating solution.

12. A method for monitoring the quality of a phosphate coating according to claim 1 wherein said metal substrate comprises an automobile body.

13. A system for monitoring the quality of a phosphate coating on a metal substrate having a large surface area, said system comprising:
   (a) a phosphating tank containing a phosphating solution in which said metal substrate having a large surface area is immersed to apply a phosphate coating thereon;
   (b) at least one counter-electrode located in contact with said phosphating solution;
   (c) means for applying a selected dc current or potential between said metal substrate and said counter electrode while said metal substrate is immersed in said phosphating solution;

(d) means for superimposing a constant ac signal on said dc potential or current applied between said metal surface and said counter electrode, said ac signal having a peak-to-peak potential or current, and a frequency;

(e) at least one reference electrode located in proximity to said metal substrate and located between said metal substrate and said counter electrode; and (f) means for measuring said ac potential between said metal substrate and said reference electrode, said measurement of ac potential being expressed as an ac spectra which provides a continual, real-time indication of defects in the phosphate coating applied to said metal substrate.

14. A system for monitoring the quality of a phosphate coating according to claim 13 wherein said counter-electrode surrounds said metal substrate on at least two sides and is distant from said metal substrate.

15. A system for monitoring the quality of a phosphate coating according to claim 13 wherein said counter-electrode has a relatively small surface area compared to said metal substrate and is located in close proximity to said metal substrate.

16. A system for monitoring the quality of a phosphate coating according to claim 13 wherein:
  (a) said counter-electrode has a large surface area; and wherein
  (b) multiple reference electrodes of small surface area are provided in close proximity to said substrate and uniformly dispersed over said large surface area of said substrate.

17. A system for monitoring the quality of a phosphate coating according to claim 13 wherein said metal substrate comprises an automobile body.

* * * * *